US006858762B2

(12) United States Patent
Baker et al.

(10) Patent No.: US 6,858,762 B2
(45) Date of Patent: Feb. 22, 2005

(54) PROCESS FOR THE MANUFACTURE OF HALOCARBONS AND SELECTED COMPOUNDS AND AZEOTROPES WITH HF

(75) Inventors: Ralph Thomas Baker, Los Alamos, NM (US); Ralph Newton Miller, Newark, DE (US); Viacheslav Alexandrovich Petrov, Hockessin, DE (US); Velliyur Nott Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 18 days.

(21) Appl. No.: 10/460,270

(22) Filed: Jun. 12, 2003

(65) Prior Publication Data

US 2003/0208090 A1 Nov. 6, 2003

Related U.S. Application Data

(62) Division of application No. 09/638,549, filed on Aug. 14, 2000, which is a division of application No. 09/011,401, filed as application No. PCT/US96/12547 on Jul. 31, 1996, now Pat. No. 6,291,730.
(60) Provisional application No. 60/019,994, filed on Jul. 18, 1996, provisional application No. 60/014,810, filed on Apr. 4, 1996, and provisional application No. 60/001,702, filed on Aug. 1, 1995.

(51) Int. Cl.[7] .......................... C07C 17/00; C07C 17/08; C07C 19/08
(52) U.S. Cl. ........................ 570/165; 570/134; 570/164; 570/166; 570/167; 570/168; 570/169; 252/182.11; 252/182.12; 252/183.13; 252/182.32
(58) Field of Search ................................. 570/134, 164, 570/165, 166, 167, 168, 169; 252/182.11, 182.12, 182.32, 183.13; 203/67

(56) References Cited

U.S. PATENT DOCUMENTS

| 3,651,019 | A | 3/1972 | Asscher et al. ............ 260/77.2 |
| 4,944,846 | A | 7/1990 | Manzer et al. .............. 203/1 |
| 5,094,773 | A | 3/1992 | Manzer et al. .............. 252/172 |
| 5,211,817 | A | 5/1993 | Adams et al. ............... 203/82 |
| 5,276,225 | A | 1/1994 | Berthe ...................... 570/178 |
| 5,346,595 | A | 9/1994 | Clemmer et al. ............ 203/75 |
| 5,395,997 | A | 3/1995 | Van Der Puy .............. 570/167 |
| 5,409,625 | A | 4/1995 | Nappa et al. ............... 252/67 |
| 5,414,165 | A | 5/1995 | Nappa et al. ............... 570/169 |
| 5,446,217 | A | 8/1995 | Van Der Py ............... 570/156 |
| 5,461,177 | A | 10/1995 | Manzer et al. ............ 570/178 |
| 5,481,050 | A | 1/1996 | Van Der Puy .............. 570/135 |
| 5,574,192 | A | 11/1996 | Van Der Puy et al. ...... 570/167 |
| 5,616,819 | A | 4/1997 | Boyce et al. ................ 570/167 |
| 5,626,725 | A | 5/1997 | Balthasart et al. ........... 203/91 |
| 5,817,893 | A | 10/1998 | Miller et al. ................ 570/134 |
| 5,846,388 | A | 12/1998 | Tsuda et al. ................. 203/67 |
| 5,948,213 | A | 9/1999 | Miller et al. ................ 203/74 |
| 6,001,796 | A | 12/1999 | Pham et al. ................. 510/408 |
| 6,040,487 | A | 3/2000 | Baker et al. |
| 6,060,629 | A | 5/2000 | Pham et al. |
| 6,255,544 | B1 | 7/2001 | Sievert |
| 6,328,907 | B1 | 12/2001 | Nakada et al. |
| 2002/0068686 | A1 | 6/2002 | Nakada et al. |

FOREIGN PATENT DOCUMENTS

| CA | 684687 | 4/1964 | .................. 260/659 |
| CA | 2 073 533 | 1/1993 | .......... C07C/17/20 |
| CA | 2 082 844 | 5/1993 | .......... C07C/19/08 |
| EP | 0 542 290 A1 | 5/1993 | .......... C07C/17/38 |
| EP | 0 669 303 A1 | 1/1995 | .......... C07C/17/38 |
| EP | 0 676 386 A1 | 10/1995 | .......... C07C/17/38 |
| EP | 0 703 205 A1 | 3/1996 | .......... C07C/17/20 |
| EP | 0 729 932 A1 | 9/1996 | ......... C07C/17/278 |
| EP | 0 703 205 B1 | 1/1998 | .......... C07C/17/20 |
| EP | 0 885 863 A1 | 12/1998 | .......... C07C/19/08 |
| JP | 9085/96 | 1/1996 | .......... C07C/17/38 |
| JP | 9-263553 | 10/1997 | |
| WO | WO 94/19301 | 9/1994 | .......... C07C/17/38 |
| WO | WO 94/27939 | 12/1994 | .......... C07C/17/22 |

(List continued on next page.)

OTHER PUBLICATIONS

Belbachir et al., *Makromol. Chem*, 185, 1583–1595, 1984.
Jurgen Gmehling et al., *Azeotropic Data, Part J. VCH*, Weinheim (1994) Introduction and pp. X–XXXV.
*Advances in Chemistry Series*, vol. 6, "Azeotropic Data", American Chemical Society, Jun. 1952, pp. 50–51.

*Primary Examiner*—Johann R. Richter
*Assistant Examiner*—Elvis O. Price

(57) ABSTRACT

A liquid phase process is disclosed for producing halogenated alkane adducts of the formula $CAR^1R^2CBR^3R^4$ (where A, B, $R^1$, $R^2$, $R^3$, and $R^4$ are as defined in the specification) which involves contacting a corresponding halogenated alkane, AB, with a corresponding olefin, $CR^1R^2=CR^3R^4$ in a dinitrile or cyclic carbonate ester solvent which divides the reaction mixture into two liquid phases and in the presence of a catalyst system containing (i) at least one catalyst selected from monovalent and divalent copper; and optionally (ii) a promoter selected from aromatic or aliphatic heterocyclic compounds which contain at least one carbon-nitrogen double bond in the heterocyclic ring. When hydrochlorofluorocarbons are formed, the chlorine content may be reduced by reacting the hydrochlorofluorocarbons with HF.

New compounds disclosed include $CF_3CF_2CCl_2CH_2CCl_3$, $CF_3CCl_2CH_2CH_2Cl$ and $CF_3CCl_2CH_2CHClF$. These compounds are useful as intermediates for producing hydrofluorocarbons.

Azeotropes of $CClF_2CH_2CF_3$ with HF and azeotropes of $CF_3CH_2CHF_2$ with HF are also disclosed; as are process for producing such azeotropes.

A process for purification of certain hydrofluorocarbons and/or chloro-precursors thereof from mixtures of such compounds with HF is also disclosed.

6 Claims, 1 Drawing Sheet

FOREIGN PATENT DOCUMENTS

| | | | |
|---|---|---|---|
| WO | WO 95/04021 | 2/1995 | ........... C07C/17/20 |
| WO | WO 95/04022 | 2/1995 | ........... C07C/17/23 |
| WO | WO 95/31422 | 11/1995 | |
| WO | WO 95/32935 | 12/1995 | ......... C07C/17/087 |
| WO | WO 96/01797 | 1/1996 | ........... C07C/17/20 |
| WO | WO 97/05090 | 2/1997 | ......... C07C/17/278 |
| WO | WO 97/27163 | 7/1997 | ........... C07C/19/08 |
| WO | WO 98/00381 | 1/1998 | ........... C07C/19/08 |
| WO | WO 98/31649 | 7/1998 | |

PROCESS FOR THE MANUFACTURE OF HALOCARBONS AND SELECTED COMPOUNDS AND AZEOTROPES WITH HF

This application is a division of pending U.S. patent application Ser. No. 09/638,549 filed Aug. 14, 2000, which is a division of U.S. patent application Ser. No. 09/011,401 filed Jan. 28, 1998 which issued as U.S. Pat. No. 6,291,730 and represents a national filing under 35 USC 371 of International Application No. PCT/US96/12547 filed Jul. 31, 1996, and claims the priority benefit of U.S. Provisional Application No. 60/019,994 filed Jun. 18, 1996, U.S. Provisional Application No. 60/014,810 filed Apr. 4, 1996 and U.S. Provisional Application No. 60/001,702 filed Aug. 1, 1995.

FIELD OF THE INVENTION

This invention relates to the manufacture of halogenated alkanes using the catalytic reaction of haloalkanes with halogenated olefins, compounds produced thereby, azeotropic compositions which can be obtained upon fluorination of such compounds, and use of azeotropes in separation processes.

BACKGROUND

The catalyzed radical addition of haloalkanes to olefins is a well known reaction. Typically, however, when a haloalkane (e.g., AB, where A is a substituted carbon atom and B is a halogen other than fluorine) is added to an olefin (e.g., $CH_2=CHR$) to form the saturated adduct (e.g., $CH_2ACHBR$), the products (i.e., halogenated addition compounds) also include varying amounts of telomers (e.g., $A(CH_2CHR)_nB$, where n is equal to 2 or more). For example, Canadian Patent No. 2,073,533 discloses a process for the manufacture of $CCl_3CH_2CCl_3$ by reacting carbon tetrachloride with vinylidene chloride using copper catalysts in acetonitrile. The selectivity for $CCl_3CH_2CCl_3$ with respect to converted vinylidene chloride was 87%. It has been shown in the art that the major by-product is the $C_5$ telomer, $CCl_3(CH_2CCl_2)_2Cl$. Furthermore, since the catalyzed addition of haloalkanes to olefins is done in a homogeneous medium, separation of the catalyst from the product can present difficulties. This is especially so when it is desired to run the reaction in a continuous manner.

The halogenated adducts are useful intermediates for the production of fluoroalkanes, particularly, hydrofluoroalkanes. These latter compounds are useful as refrigerants, fire extinguishants, heat transfer media, propellants, foaming agents, gaseous dielectrics, sterilant carriers, polymerization media, particulate removal fluids, carrier fluids, buffing abrasive agents, displacement drying agents and power cycle working fluids. There is an interest in developing more efficient processes for the manufacture of hydrofluoroalkanes.

SUMMARY OF THE INVENTION

A liquid phase process is provided in accordance with this invention for producing halogenated alkane adducts of the formula $CAR^1R^2CBR^3R^4$ wherein $R^1$, $R^2$, $R^3$, and $R^4$ are each independently selected from the group consisting of H, Br, Cl, F, $C_1-C_6$ alkyl, CN, $CO_2CH_3$, $CH_2Cl$, and aryl (e.g., phenyl), provided that when either $R^3$ or $R^4$ is selected from the group consisting of $C_3-C_6$ alkyl, CN, $CO_2CH_3$, $CH_2Cl$, and aryl, then $R^1$, $R^2$, and the other of $R^3$ and $R^4$ are H, and when $R^3$ and $R^4$ are selected from the group consisting of Cl, F, $CH_3$ and $C_2H_5$, then $R^1$ and $R^2$ are H, and when either $R^1$ or $R^2$ and either $R^3$ or $R^4$ are selected from the group consisting of Cl, F, $CH_3$ and $C_2H_5$, then the other of $R^1$ and $R^2$ and the other of $R^3$ and $R^4$ are H; A is selected from the group consisting of $CX_3$, $CH_{3-a}X_a$, $C_nH_{(2n+1)-b}X_b$ and $CH_cX_{2-c}R$, where R is $C_nH_{(2n+1)-b}X_b$ (e.g., $CF_3$ and $CCl_2CF_3$), each X is independently selected from the group consisting of Br, F, Cl and I, a is an integer from 0 to 3, n is an integer from 1 to 6, b is an integer from 1 to 2n+1, and c is an integer from 0 to 1; and B is selected from the group consisting of Br, Cl and I; provided that (1) when A is $CX_3$ then only one of X is I, (2) when A is $CH_{3-a}X_a$, then each X is B and a is 2 when B is Br or Cl, and a is an integer from 0 to 2 when B is I, and (3) when A is $C_nH_{(2n+1)-b}X_b$, then each X is independently selected from Cl and F, and B is I. The process comprises contacting a halogenated alkane of the formula AB (where A and B are as indicated above) with an olefin of the formula $CR^1R^2=CR^3R^4$ (where $R^1$, $R^2$, $R^3$ and $R^4$ are as indicated above) in a dinitrile or cyclic carbonate ester solvent which divides the reaction mixture into two liquid phases and in the presence of a catalyst system containing (i) at least one catalyst selected from the group consisting of monovalent and divalent copper; and optionally (ii) a promoter selected from the group consisting of aromatic or aliphatic heterocyclic compounds which contain at least one carbon-nitrogen double bond in the heterocyclic ring.

This invention further provides a process for producing hydrofluoroalkanes (e.g., $CF_3CH_2CHF_2$). This process comprises (a) producing a halogenated alkane adduct (e.g., $CCl_3CH_2CHCl_2$) by reacting AB (e.g., $CCl_4$) and $CR^1R^2=CR^3R^4$ (e.g., $CH_2=CHCl$) as indicated above (provided that $R^1$, $R^2$, $R^3$ and $R^4$ are independently selected from H, $CH_3$, $C_2H_5$, Cl and F, B and X are Cl and at least one of AB and $CR^1R^2=CR^3R^4$ contains hydrogen), and (b) reacting the adduct produced in (a) with HF.

This invention also provides a process for the purification of at least one compound of the formula $CA^1R^5R^6CB^1R^7R^8$ from a mixture comprising HF and said at least one compound, wherein $A^1$ is selected from the group consisting of $CH_{3-a}X^1_a$ and $CH_cX^1_{2-c}R^9$ where $R^9$ is $C_nH_{(2n+1)-b}X^1_b$, each $X^1$ and $B^1$ is independently selected from the group consisting of Cl and F, $R^5$, $R^6$, $R^7$, and $R^8$ are each independently selected from the group consisting of H, Cl and F, and a, b, c and n are as defined above, provided that at least one of $A^1$, $R^5$, $R^6$, $R^7$, or $R^8$ comprises hydrogen. The purification process comprises (a) subjecting the mixture of HF and said at least one compound to a distillation step in which a composition enriched in either (i) HF or (ii) said at least one compound is removed as a first distillate with the bottoms being enriched in the other of said components (i) or (ii); (b) subjecting said first distillate to an additional distillation conducted at a different pressure in which the component enriched as bottoms in (a) is removed as a second distillate with the bottoms of the additional distillation enriched in the component enriched in the first distillate; and (c) recovering at least one compound of the formula $CA^1R^5R^6CB^1R^7R^8$ essentially free of HF as bottoms from either the distillation of (a) or the distillation of (b).

New compounds provided in accordance with this invention include $CF_3CF_2CCl_2CH_2CCl_3$, $CF_3CCl_2CH_2CH_2Cl$ and $CF_3CCl_2CH_2CHClF$. These compounds are useful as intermediates for producing hydrofluorocarbons.

New compositions produced by this invention include azeotropic compositions of $CF_3CH_2CHF_2$ with HF and azeotropic compositions of $CF_3CH_2CClF_2$ with HF. A composition comprising from about 44 to 84 mole percent HF and from about 56 to 16 mole percent $CF_3CH_2CHF_2$ is provided which, when the temperature is adjusted within the range of −50° C. to 130° C., exhibits a relative volatility of about 1 at a pressure within the range of 5.5 kPa to 3850 kPa. Also, a composition comprising from about 63.0 to 90.1 mole percent HF and from about 37.0 to 9.9 mole percent $CF_3CH_2CClF_2$ is provided which, when the temperature is adjusted within the range of −40° C. to 110° C., exhibits a relative volatility of about 1 at a pressure within the range of about 9.3 kPa to 2194 kPa.

DETAILED DESCRIPTION

Figure 1:
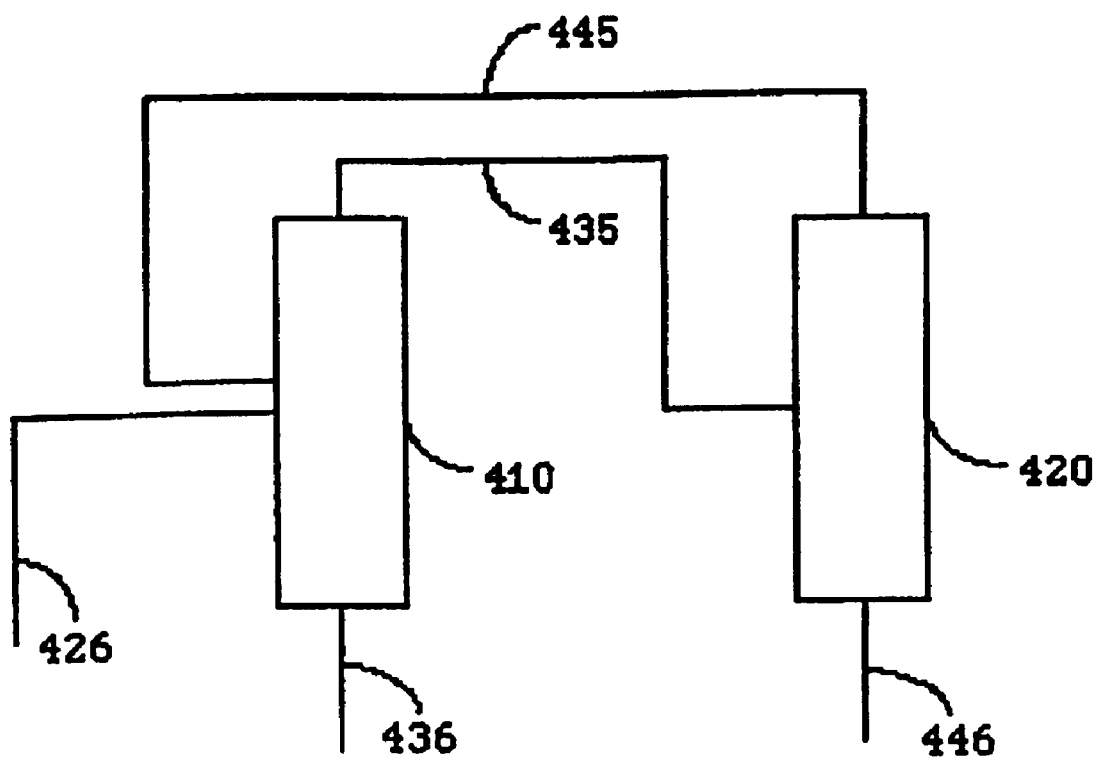
FIG. 1 is a schematic flow diagram of an embodiment of the purification process of this invention, namely, an azeotrope separation process.

The present invention relates to the addition of halogenated alkanes to unsaturated compounds to form an adduct. Specifically, this invention relates to the addition of a halogenated alkane of the general formula AB to an unsaturated compound $CR^1R^2\!=\!CR^3R^4$ to form a corresponding adduct $CAR^1R^2CBR^3R^4$ in the presence of a copper catalyst ($Cu^+$ and/or $Cu^{++}$) in a suitable solvent (a dinitrile or cyclic carbonate ester solvent). A promoter containing a C=N ring bond may also be advantageously used.

The addition of saturated, halogenated alkanes to alkenes to form adducts is known in the art. A wide range of saturated, halogenated alkanes may be used in the process of the invention. Examples of suitable saturated, halogenated alkanes are given by Walling and Huyser in Tables V, VI, VII, and VIII in Chapter 3 of Organic Reactions, Vol. 13 (1963).

Halogenated alkanes, AB, that are particularly useful for the process of this invention include certain compounds where A is selected from the group consisting of $CX_3$, $CH_{3-a}X_a$, $C_nH_{(2+1)-b}X_b$ and $CH_cX_{2-c}R$ where each X is Br, Cl or I and R is $C_nH_{(2n+1)-b}X_b$ (e.g., $CF_3$ and $CCl_2CF_3$); and B is Br, F, Cl or I. Included are compounds where A is $CX_3$ and only one of X is I. Also included are compounds where A is $CH_{3-a}X_a$ where X is B and where when X is Br or Cl, a is 2, and when X is I, a is an integer from 0 to 2. Also included the compounds where A is $C_nH_{(2n+1)-b}X_b$, where each X is independently selected from Cl and F, n is an integer from 1 to 6, b is an integer from 1 to 2n+1, and B is I. Also included are compounds where A is $CH_cX_{2-c}R$ wherein c is an integer from 0 to 1. Examples of saturated, halogenated alkanes suitable for the process of this invention include $CCl_4$, $CBrCl_3$, $CCl_2FCCl_2F$, $CCl_3CF_3$, $CCl_3CF_2CF_3$, $CCl_3CH_2CCl_3$, $CCl_3CH_2CF_3$, $CCl_3CF_2CClF_2$, $CF_3I$, $CF_3CF_2I$, $CF_3CFICF_3$ and $CF_3CF_2CF_2I$.

A wide range or alkenes may be used in the process or the invention. Examples of suitable alkenes are given by Walling and Huyser in Tables V, VI, VII, and VIII in Chapter 3 of Organic Reactions, Vol. 13 (1963). Examples of alkenes suitable for the process of this invention include $CH_2\!=\!CH_2$, $CH_2\!=\!CHCl$, $CH_2\!=\!CHF$, $CHCl\!=\!CHCl$, $CH_2\!=\!CCl_2$, $CH_2\!=\!CF_2$, $CH_2\!=\!CHCH_3$, $CH_2\!=\!CHCH_2Cl$, and $CH_2\!=\!CHC_6H_5$.

The addition of halogenated alkanes to alkenes to form the corresponding adducts is catalyzed by copper compounds in the +1 or +2 oxidation state. Preferred copper compounds for the process of this invention include copper (I) chloride, copper(II) chloride, copper(I) bromide, copper (II) bromide, copper(I) iodide, copper(II)acetate and copper (I) sulfate. The catalysts are preferably anhydrous; and preferably, the addition is done under substantially anhydrous conditions in the substantial absence of oxygen. Without wishing to be bound by theory, it is believed that the effect of the catalyst is to enhance the yield of the 1:1 addition product (i.e., the adduct) of the halogenated alkanes to the alkene relative to higher molecular weight telomers that are known in the art.

The copper catalyst for the process of the invention may, if desired, be promoted by certain heterocyclic compounds. Suitable promoters include those selected from the group consisting of imidazoles, imidazolines, oxadiazoles, oxazoles, oxazolines, isoxazoles, thiazoles, thiazolines, pyrrolines, pyridines, trihydropyrimidines, pyrazoles, triazoles, triazolium salts, isothiazoles, tetrazoles, tetrazolium salts, thiadiazoles, pyridazines, pyrazines, oxazines and dihydrooxazine. Preferred promoters include those selected from the group having Formula (I) or Formula (II) as follows:

(I)

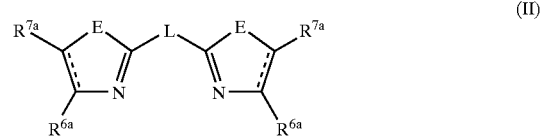

(II)

where E is selected from —O—, —S—, —Se—, —$CH_2$— and —N($R^{8a}$)—; $R^{5a}$ is selected from the group consisting of $CH_3$ and $C_2H_5$ (and is preferably $CH_3$); $R^{6a}$ and $R^{7a}$ are selected from the group consisting of H, $CH_3$, $C_6H_5$ (i.e., phenyl), $CH_2C_6H_5$, $CH(CH_3)_2$, and fused phenyl; L is selected from the group consisting of —O—, —S—, —Se—, —N($R^{8a}$)—, —$C_6H_4$—, 2,6-pyridyl, —$OC_6H_4$—$C_6H_4O$—, —$CH_2CH_2OCH_2CH_2$— and —$(CH_2)_p$— where p is an integer from 0 to 6; and each $R^{8a}$ is selected from the group consisting of H and $C_mH_{2m+1}$ where m is an integer from 1 to 6. The bond between each pair of carbon atoms respectively attached to $R^{6a}$ and $R^{7a}$ (as represented by the dashed bond lines in Formula (I) and Formula (II) can be either a single or a double bond. Of note are compounds of Formula (II) which are optically active. Without wishing to be bound by theory, it is believed that the effect of the promoter is to enhance the rate and selectivity of the reaction. Frequently, use of the promoter will enable operation of the reaction at a lower temperature, and with an acceptable rate, than would be possible in the absence of the promoter. Reference is made to U.S. Patent Application Serial No. 60/001,702, a priority document for PCT International Publication No. 97/05090, which is hereby incorporated by reference, for further disclosure relating to such promoters.

The process of this invention is carried out in the presence of a solvent. Typically, the solvents of this invention divide the reaction mixture into two liquid phases. Suitable solvents for the process of the invention thus include those which not only promote the formation of the 1:1 adduct, but also divide the reaction mixture into two liquid phases. The product addition compound is preferably concentrated in the lower liquid phase, while the solvent and catalyst are preferably concentrated in the top liquid phase. Preferred solvents for the process of this invention include dinitriles and cyclic carbonate esters. These solvents are commercially available. Examples of solvents for the process of this invention include ethylene carbonate, propylene carbonate, butylene carbonate, 1,2-cyclohexane carbonate, malononitrile, succinonitrile, ethyl succinonitrile, glutaronitrile, methyl glutaronitrile, adiponitrile, pimelonitrile, suberonitrile, and mixtures thereof. Preferred solvents for the process of the invention are adiponitrile, glutaronitrile, methyl glutaronitrile, and propylene carbonate.

The choice of the solvent for the process of the invention will require some experimentation, as the solubility characteristics of the starting materials and adducts need to be considered to develop the required two phase system. However, the preferred solvents noted above provide the desired two phase systems for a number of addition reactions as illustrated in the Examples.

Another important criterion for the choice of solvent is the boiling point of the solvent relative to that of the desired addition compounds. It is preferred that the boiling point of the solvent be higher than the boiling point of the adduct so that easy separation of the adduct from the solvent may be made by distillation.

Another important criterion for the choice of solvent is that it serve as a solvent for the catalyst or catalyst/promoter mixture at the reaction temperature or below.

The catalyst system comprising the copper compound and the solvent, (and optionally the promoter when present as disclosed above) can be prepared in advance in a suitable mixing vessel and then added to the reaction mixture. Alternatively, the individual components of the catalyst system can be added individually to the reactor.

The process of the present invention is suitably conducted at a temperature in the range of from about 90° C. to 150° C., preferably from about 100° C. to about 140° C., and most preferably, from about 110° C. to 130° C.

The pressure of the process is not critical and can be subatmospheric, atmospheric or superatmospheric, preferably, superatmospheric. The pressure in the system is frequently governed by the vapor pressures of the reactants at the temperature of the reaction. The reaction may be carried out under a pressure of nitrogen or other inert gas diluent.

While the use of a copper catalyst tends to minimize the formation of higher telomers as known in the art, the formation of 2:1 and higher adducts (i.e., those addition compounds containing more than one mole of alkene per mole of adduct) can be further controlled by manipulating reaction variables such as the molar ratio of the halogenated alkane to the alkene. Higher molar ratios of halogenated alkane to alkene and dilution of the alkene reduce telomer formation. This can be accomplished by continuously feeding the alkene or mixture of the alkene and of the halogenated alkane to a heel of the halogenated alkane and catalyst mixture.

The total amount of copper catalyst used in the reaction of this invention is typically at least about 5 mmoles, preferably from about 5 mmole to 700 mmoles, and more preferably from about 10 mmoles to 100 mmoles, per mole of alkene used.

When used, the amount of optional promoter used in the reaction of this invention is typically at least an amount sufficient to provide 2 mmol of heterocyclic ring which contains carbon-nitrogen double bonding per mmol of copper catalyst. For example, typically at least about 2 moles of Formula (I) promoter or about 1 mole of Formula (II) promoter is typically used per mole of copper catalyst.

The amount of halogenated alkane used in the reaction of this invention is typically at least about 1 mole, and preferably from about 2 moles to 10 moles, per mole of alkene used.

The amount of solvent used in the reaction of this invention is typically at least about 5 moles, and preferably from about 10 moles to 100 moles, per mole of copper catalyst used.

The process of the present invention facilitates easy separation of the 1:1 addition product of the halogenated alkane to the alkene by taking advantage of the two phase nature of reaction mixture of this invention. That is, the desired 1:1 addition product tends to accumulate in the lower of the two liquid layers while the solvent and the catalyst tend to accumulate in the upper layer. The upper and lower layers may be separated continuously in a separation zone (e.g., a decanter) as is known in the art or on a batch basis by allowing the phases to separate in the reactor and removing the lower layer from the bottom of the vessel. The catalyst and solvent in the upper layer may be re-used for subsequent reactions as illustrated in Examples 3, 4, and 5.

If the reaction is being operated in a continuous manner or if multiple batches are being run with the same catalyst charge, a gradual loss of reaction rate may be observed. A satisfactory reaction rate can often be restored by addition of promoter to the reaction.

The desired addition product may be separated from any alkene starting material, alkane starting material, solvent, and any higher telomer products by conventional techniques such as distillation. The low boiling fraction will typically be the starting halogenated alkane and the alkene which may be recovered and recycled to the reactor. Higher boiling material will comprise the solvent and any higher boiling telomer by-products. The higher boiling phase may be further refined and the solvent recycled to the reactor. The separation of the two liquid phases in the reactor may be done at temperatures between the reaction temperature and ambient temperature; cooling the reaction mixture lower than room temperature is usually not necessary.

The reaction zone and its associated feed lines, effluent lines and associated units should be constructed of materials resistant to corrosion. Typical materials of construction include steel reactors lined with poly(tetrafluoroethylene) or glass and glass reactors.

The addition compounds that comprise the products of this invention are useful as intermediates for the formation of hydrofluoroalkanes. (Novel compounds provided herein include $CF_3CF_2CCl_2CH_2CCl_3$, which may be made by reacting $CF_3CF_2CCl_3$ with $CH_2=CCl_2$; $CF_3CCl_2CH_2CH_2Cl$, which may be made by reacting $CF_3CCl_3$ with $CH_2=CH_2$ and $CF_3CCl_2CH_2CHClF$, which may be made by reacting $CF_3CCl_3$ with $CH_2=CHF$). These addition compounds can be reacted with hydrogen fluoride in either the liquid or vapor phase in the presence of a suitable fluorination catalyst.

In the liquid phase, the addition compounds can be reacted with HF in the presence of catalysts selected from the halides of antimony, molybdenum, niobium, tantalum, tin and titanium, and mixtures thereof, preferably, antimony, niobium and tantalum. The temperature of the reaction can be in the range of 50° C. to 175° C., preferably, 60° C. to 150° C. The pressure is selected so that the the reaction medium is maintained in the liquid state, typically between 101 kPa and 5000 kPa, preferably, 1135 kPa to 3203 kPa. For example, 1,1,1,3,3,3-hexachloropropane (HCC-230fa) can be reacted with HF in the liquid phase using halides, fluorosulfonates or triflates of antimony, molybdenum, niobium, tantalum, tin or titanium, or mixtures thereof as catalysts to produce 1,1,1,3,3,3-hexafluoropropane (HFC-236fa). 1-Chloro-1,1,3,3,3-pentafluoropropane (HCFC-235fa) can also be prepared from HCC-230fa (e.g., by reacting said $CCl_3CH_2CCl_3$ with HF). The reaction products may be separated by conventional techniques such as distillation. Azeotropic compositions of HCFC-235fa and HF can be produced in this manner; and the HCFC-235fa can be further reacted with HF to produce HFC-236fa. The HCFC-235fa product can also be hydrodechlorinated using a hydrodehalogenation catalyst to produce 1,1,1,3,3-pentafluoropropane (HFC-245fa). Palladium on acid-washed carbon is a preferred catalyst for the conversion of HCFC-235fa to HFC-245fa.

In another embodiment of this invention carbon tetrachloride can be reacted with vinyl chloride to produce the adduct 1,1,1,3,3-pentachloropropane (i.e., $CCl_3CH_2CHCl_2$ or HCC-240fa). $CCl_3CH_2CHCl_2$ can then be reacted with HF (e.g., in the liquid phase using the process described above) to produce $CF_3CH_2CHF_2$. The reaction products may be separated by conventional techniques such as distillation. Azeotropic compositions of HFC-245fa and HF can be produced in this manner.

In the vapor phase, the addition compounds can be reacted with HF in the presence of catalysts comprising trivalent chomium. Catalysts prepared by pyrolysis of $(NH_4)_2Cr_2O_7$ to produce $Cr_2O_3$ and pretreated with HF and catalysts prepared by pretreating $Cr_2O_3$ having a surface area greater than about 200 $m^2/g$ with HF are preferred. The temperature of the reaction can be in the range of 200° C. to 400° C., preferably, 250° C. to 375° C. The pressure is not critical and is selected so that the reaction starting materials and products are maintained in the vapor state at the operating temperature. For example, it has recently been disclosed in U.S. Pat. No. 5,414,165 that 1,1,1,3,3,3-hexafluoropropane may be prepared in high yield from 1,1,1,3,3,3-hexachloropropane by a vapor phase hydrofluorination process in the presence of a trivalent chromium catalyst.

Although the 1:1 addition compounds of the halogenated alkanes to the alkenes are the preferred products, the 2:1 adducts may also be useful.

Hydrofluorocarbons such as $CF_3CH_2CHF_2$ and hydrochlorofluorocarbons such as $CF_3CH_2CClF_2$ form azeotropes with HF; and conventional decantation/distillation may be employed if further purification of the hydrofluorocarbons is desired.

Moreover, a process for purification as provided herein may also be used. Hydrofluoroalkanes and chloro-precursors thereof provided in the process for producing halogenated alkane adducts described above and/or the process for producing hydrofluoroalkanes described above include compounds of the formula $CA^1R^5R^6CB^1R^7R^8$. Typically, these compounds form azeotropes with HF, and the process for purification provided herein may be advantageously used for purification of a compound of said formula from its HF azeotrope (e.g., a binary azeotrope of a compound having the formula $CA^1R^5R^6CB^1R^7R^8$ with HF). Examples of compounds which can be purified from their binary azeotropes with HF by this purification process include compounds selected from the group consisting of $CF_3CH_2CHF_2$, $CF_3CH_2CF_3$, $CF_3CH_2CClF_2$, $CHCl_2CH_2CF_3$, $CHClFCH_2CClF_2$, $CHClFCH_2CF_3$, and $CHF_2CH_2CClF_2$.

An azeotrope is a liquid mixture that exhibits a maximum or minimum boiling point relative to the boiling points of surrounding mixture compositions. A characteristic of minimum boiling azeotropes is that the bulk liquid composition is the same as the vapor compositions in equilibrium therewith, and distillation is ineffective as a separation technique. It has been found, for example, that $CF_3CH_2CHF_2$ (HFC-245fa) and HF form a minimum boiling azeotrope. This azeotrope can be produced as a co-product with HFC-245fa. As discussed further below, compositions may be formed which consist essentially of azeotropic combinations of hydrogen fluoride with HFC-245fa. These include a composition consisting essentially of from about 44 to 84 mole percent HF and from about 56 to 16 mole percent HFC-245fa (which forms an azeotrope boiling at a temperature between −50° C. and about 130° C. at a pressure between about 5.5 kPa and about 3850 kPa). In other words, when the temperature is adjusted within the range of −50° C. to 130° C., these compositions exhibit a relative volatility of about 1 (e.g., between 0.9 and 1.1) at a pressure within the range of 5.5 kPa to 3850 kPa. The hydrofluorocarbons (e.g., HFC-245fa) can be separated from the HF in such azeotropes by conventional means such as neutralization and decantation. However, azeotropic compositions of the hydrofluorocarbons and HF (e.g., an azeotrope recovered by distillation of hydrogenolysis reactor effluent) are useful as recycle to a fluorination reactor, where the recycled HF can function as a reactant and the recycled HFC-245fa can function to moderate the temperature effect of the heat of reaction. It will also be apparent to one of ordinary skill in the art that distillation including azeotropes with HF can typically be run under more convenient conditions than distillation without HF (e.g., where HF is removed prior to distillation).

It has also been found that $CClF_2CH_2CF_3$ (HCFC-235fa) and HF form a minimum boiling azeotrope. This azeotrope can be produced as a co-product with HCFC-235fa. As discussed further below, compositions may be formed which consist essentially of azeotropic combinations of hydrogen fluoride with HCFC-235fa. These include a composition consisting essentially of from about 63.0 to 90.1 mole percent HF and from about 37.0 to 9.9 mole percent HCFC-235fa (which forms an azeotrope boiling at a temperature between −40° C. and about 110° C. at a pressure between about 9.3 kPa and about 2194 kPa). In other words, when the temperature is adjusted within the range of −40° C. to 110° C., these compositions exhibit a relative volatility of about 1 (e.g., between 0.9 and 1.1) at a pressure within the range of about 9.3 kPa to 2194 kPa. The hydrofluorocarbons (e.g., HCFC-235fa) can be separated from the HF in such azeotropes by conventional means such as neutralization and decantation. However, azeotropic compositions of the hydrofluorocarbons and HF (e.g., an azeotrope recovered by distillation of hydrogenolysis reactor effluent) are useful as recycle to a fluorination reactor, where the recycled HF can function as a reactant and the recycled HCFC-235fa can further react to provide HFC-236fa and can function to moderate the temperature effect of the heat of reaction. It will also be apparent to one of ordinary skill in the art that distillation including azeotropes with HF can typically be run under more convenient conditions than distillation without HF (e.g., where HF is removed prior to distillation).

HFC-245fa/HF Azeotrope

As noted above, the present invention provides a composition which consists essentially of hydrogen fluoride and an effective amount of a $CF_3CH_2CHF_2$ to form an azeotropic combination with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the individual components, and which will provide a vapor composition essentially identical to the liquid composition undergoing boiling.

For the purpose of this discussion, azeotrope-like composition means a composition which behaves like an azeotrope (i.e., has constant-boiling characteristics or a tendency not to fractionate upon boiling or evaporation). Thus, the composition of the vapor formed during boiling or evaporation of such compositions is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte, Ind. Eng. Chem. Process Des. Dev. 1980, 19, pp 432–439). Experimental identification of azeotropic compositions involving the same components may be used to confirm the accuracy of such calculations and/or to modify the calculations for azeotropic compositions at the same or other temperatures and pressures.

It has been found that azeotropes of HF and HFC-245fa are formed at a variety of temperatures and pressures. At a pressure of 7.60 psia (52.4 kPa) and −10° C., the azeotrope vapor composition was found to be about 74.0 mole percent HF and about 26.0 mole percent HFC-245fa. At a pressure of 26.7 psia (184 kPa) and 20° C., the azeotrope vapor composition was found to be about 66.1 mole percent HF and 33.9 mole percent HFC-245fa. Based upon the above findings, it has been calculated that an azeotropic composition of about 84.4 mole percent HF and about 15.6 mole percent HFC-245fa can be formed at −50° C. and 0.80 psia (5.5 kPa) and an azeotropic composition of about 44.1 mole percent HF and about 55.9 mole percent HFC-245fa can be formed at 130° C. and 559 psia (3853 kPa). Accordingly, the present invention provides an azeotrope or azeotrope-like composition consisting essentially of from about 84.4 to 44.1 mole percent HF and from about 15.6 to 55.9 mole percent HFC-245fa, said composition having a boiling point from about −50° C. at 5.5 kPa to about 130° C. at 3853 kPa.

HCFC-235fa/HF Azeotrope

It has been found that azeotropes of HF and HCFC-235fa are formed at a variety of temperatures and pressures. At a pressure of 33.6 psia (232 kPa) and 30° C., the azeotrope vapor composition was found to be about 78.4 mole percent HF and about 21.6 mole percent HCFC-235fa. At a pressure of 87.1 psia (600 kPa) and 60° C., the azeotrope vapor composition was found to be about 72.4 mole percent HF and 27.6 mole percent HCFC-235fa. Based upon the above findings, it has been calculated that an azeotropic composition of about 90.1 mole percent HF and about 9.9 mole percent HCFC-235fa can be formed at 40° C. and 1.36 psia (9.4 kPa) and an azeotropic composition of about 63.0 mole percent HF and about 37.0 mole percent HCFC-235fa can be formed at 110° C. and 318 psia (2192 kPa). Accordingly, the present invention provides an azeotrope or azeotrope-like composition consisting essentially of from about 90.1 to 63.0 mole percent HF and from about 9.9 to 37.0 mole percent HCFC-235fa, said composition having a boiling point from about −40° C. at 9.4 kPa to about 110° C. at 2192 kPa. intermediates.

The present invention also provides a process for the separation of an azeotropic mixture of hydrogen fluoride (HF) and 1,1,1,3,3-pentafluoropropane (i.e., $CF_3CH_2CHF_2$ or HFC-245fa) to obtain $CF_3CH_2CHF_2$ essentially free of HF. For example, (a) an initial mixture wherein the molar ratio of HF to HFC-245fa is greater than about 1.2:1 can be separated by azeotropic distillation in a first distillation column wherein the temperature of the feed inlet to said distillation column is about 97.3° C. and the pressure is about 166.1 psia (1145 kPa), with azeotrope products containing HF and HFC-245fa being removed as distillate from the top of the first distillation column and any high boilers and HF being removed from the bottom of the first distillation column; (b) said azeotrope products from the top of the column in step (a) can be fed to a second distillation column wherein the temperature of the feed inlet to said second distillation column is about 19° C. and the pressure is about 21.2 psia (146 kPa), with azeotrope products containing HF and HFC-245fa being removed as distillate from the top of the second distillation column; and (c) essentially pure HFC-245fa can be recovered from the bottom of the second distillation column in step (b). Optionally, said azeotrope products containing HF and HFC-245fa removed from the top of the second distillation column can be recycled as feed to step (a).

In another embodiment of this invention, (a) an initial mixture wherein the molar ratio of HF to HFC-245fa is about 1.2:1 or less, can be separated by azeotropic distillation in a first distillation column wherein the temperature of the feed inlet to said distillation column is about 19° C. and the pressure is about 21.2 psia (146 kPa) with azeotrope products containing HF and HFC-245fa being removed as distillate from the top of the first distillation column; (b) said azeotrope products from the top of the column in step (a) can be fed to a second distillation column wherein the temperature of the feed inlet to said second distillation column is about 97.3° C. and the pressure is about 166.1 psia (1145 kPa), with azeotrope products containing HF and HFC-245fa being removed as distillate from the top of the second distillation column and any high boilers and HF being removed from the bottom of the second distillation column; and (c) essentially pure HFC-245fa can be recovered from the bottom of the first distillation column. Optionally, said azeotrope products containing HF and HFC-245fa from the top of the second distillation column can be recycled as feed to step (a).

The above embodiment of this invention involves azeotropic distillation of mixtures of HF and $CF_3CH_2CHF_2$ (HFC-245fa). The product mixtures distilled in accordance with this invention can be obtained from a variety of sources. These sources include product mixtures from the following sequence of reactions.

CCl$_3$CH$_2$CHCl$_2$ (HCC-240fa), a compound known in the art, can be prepared from the reaction of carbon tetrachloride with vinyl chloride as disclosed in U.S. Pat. No. 3,651,019. HCC-240fa can then be reacted with HF in the vapor or liquid phase to afford HFC-245fa. The fluorination reactor products typically include CHCl=CHCF$_3$ (HCFC-1233zd), CHCl$_2$CH$_2$CF$_3$ (HCFC-243fa), CHClFCH$_2$CClF$_2$ (HCFC-243fb), CHClFCH$_2$CF$_3$ (HCFC-244fa), CHF$_2$CH$_2$CClF$_2$ (HCFC-244fb), CF$_3$CH$_2$CHF$_2$ (HFC-245fa), HCl and HF. HCFC-243fa, HCFC-243fb, HCFC-244fa and HCFC-244fb likely form azeotropes with HF.

While the initial mixture treated in accordance with the present invention can be obtained from a variety of sources, an advantageous use of the instant invention resides in treating the effluent mixtures from the preparation of HFC-245fa as described above. Generally the reaction effuents have a molar ratio of HF:HFC-245fa from about 0.1:1 to 100:1. The preferred HF:HFC-245fa molar ratio is about 1:1 to about 10:1 for vapor phase reactions and about 1:1 to about 50:1 for liquid phase reactions to achieve maximum benefit from the instant process. When the initial mixture treated in accordance with the invention also contains HCl and possibly other low-boilers, the HCl and other low-boilers are typically removed in another distillation column before feeding the mixture to the azeotrope separation columns.

High-boilers, if present, can be removed in an independent distillation column after separation of the HF from the HFC-245fa.

FIG. 1 is illustrative of one method of practicing this invention. Referring to FIG. 1, a feed mixture derived from an HFC-245fa synthesis reactor comprising HF and HFC-245fa, wherein the molar ratio of HF:HFC-245fa is greater than about 1.2:1, from an HCl removal column (not shown), is passed through line (426) to a multiple stage distillation column (410), operating at a temperature of about 75° C. and a pressure of about 1135 kPa. The bottoms of the distillation column (410), which contains HF at a temperature of about 104° C. and a pressure of about 1156 kPa is removed through line (436) and can be recycled back to the HFC-245fa synthesis reactor. The distillate from column (410) which contains HF/HFC-245fa azeotrope (HF:HFC-245fa molar ratio is about 1.2:1) is removed from the top of the column (410) and sent through line (435) to column (420). The distillate from column (420) which contains HF/HFC-245fa azeotrope (HF:HFC-245fa molar ratio is about 2.1:1) and is at a temperature of about 12° C. and a pressure of about 136 kPa is removed from the top of column (420) and is recycled through line (445) to column (410). The bottoms of the distillation column (420) which contains essentially pure HFC-245fa at about 26.5° C. and 156 kPa is removed from the bottom of column (420) through line (446). In this embodiment, column (410) operates as a high pressure column. Column (420) operates as a low pressure column.

In another embodiment of this invention the pressures of the columns are reversed. Again referring to FIG. 1, a feed mixture derived from an HFC-245fa synthesis reactor comprising HF and HFC-245fa, wherein the molar ratio of HF:HFC-245fa is about 1.2:1 or less, from an HCl removal column (not shown), is passed through line (426) to a multiple stage distillation column (410), operating at a temperature of about 12° C. and a pressure of about 136 kPa. The bottoms of the distillation column (410) which contains essentially pure HFC-245fa at about 28.5° C. and 156 kPa is removed from the bottom of column (410) through line (436). The distillate from column (410) which contains HF/HFC-245fa azeotrope (HF:HFC-245fa molar ratio is about 2.1:1) at a temperature of about 12° C. and a pressure of about 140 kPa is removed from the top of column (410) and sent through line (435) to column (420). The distillate from column (420) which contains HF/HFC-245fa azeotrope (HF:HFC-245fa molar ratio is about 1.2:1) and is at a temperature of about 79° C. and a pressure of about 1135 kPa is removed from the top of column (420) and is recycled through line (445) to column (410). The bottoms of the distillation column (420) which contains HF a temperature of about 104° C. and a pressure of about 1156 kPa is removed through line (446) and can be recycled back to the HFC-245fa synthesis reactor. In this embodiment column (410) operates as a low pressure column. Column (420) operates as a high pressure column.

While specific temperatures, pressures and molar ratios were recited in the above two embodiments, variation of the pressure will also cause shifts in the HF:HFC-245fa molar ratios and in the distillation temperatures. The use of a "low" and a "high" pressure column in tandem as described above can be used to separate HF from HFC-245fa for any HF:HFC-245fa ratio (e.g., from 0.1:1 to 100:1).

The present invention further provides a process for the separation an azeotropic mixture of hydrogen fluoride (HF) and 1,1,1,3,3-pentafluoro-3-chloropropane (i.e., CF$_3$CH$_2$CClF$_2$ or HFC-235fa) to obtain CF$_3$CH$_2$CClF$_2$ essentially free of HF. For example, (a) an initial mixture wherein the molar ratio of HF to HFC-235fa is greater than about 2:1 can be separated by azeotropic distillation in a first distillation column wherein the temperature of the feed inlet to said distillation column is about 109° C. and the pressure is about 216.2 psia (1490 kPa), with azeotrope products containing HF and HFC-235fa being removed as distillate from the top of the first distillation column and any high boilers and HF being removed from the bottom of the first distillation column; (b) said azeotrope products from the top of the column in step (a) can be fed to a second distillation column wherein the temperature of the feed inlet to said second distillation column is about 29° C. and the pressure is about 21.2 psia (146 kPa), with azeotrope products containing HF and HFC-235fa being removed as distillate from the top of the second distillation column; and (c) essentially pure HFC-235fa can be recovered from the bottom of the second distillation column in step (b). Optionally, said azeotrope products containing HF and HFC-235fa removed from the top of the second distillation column can be recycled as feed to step (a).

In another embodiment of this invention, (a) an initial mixture wherein the molar ratio of HF to HFC-235fa is about 4:1 or less, can be separated by azeotropic distillation in a first distillation column wherein the temperature of the feed inlet to said distillation column is about 28° C. and the pressure is about 21.2 psia (146 kPa) with azeotrope products containing HF and HFC-235fa being removed as distillate from the top of the first distillation column; (b) said azeotrope products from the top of the column in step (a) can be fed to a second distillation column wherein the temperature of the feed inlet to said second distillation column is about 110° C. and the pressure is about 216.2 psia (1490 kPa), with azeotrope products containing HF and HFC-235fa being removed as distillate from the top of the second distillation column and any high boilers and HF being removed from the bottom of the second distillation column; and (c) essentially pure HFC-235fa can be recovered from the bottom of the first distillation column. Optionally, said azeotrope products containing HF and HFC-235fa from the top of the second distillation column can be recycled as feed to step (a).

The initial mixture of HF and HFC-235fa treated in accordance with the present invention can be obtained from a variety of sources. Generally the reaction effuents have a molar ratio of HF:HFC-235fa from about 0.1:1 to 100:1. The preferred HF:HFC-235fa molar ratio is from about 0.1:1 to about 10:1 for vapor phase reactions and about 1:1 to about 50:1 for liquid phase reactions to achieve maximum benefit from the instant process. When the initial mixture treated in accordance with the invention also contains HCl and possibly other low-boilers, the HCl and other low-boilers are typically removed in another distillation column before feeding the mixture to the azeotrope separation columns.

High-boilers, if present, can be removed in an independent distillation column after separation of the HF from the HFC-235fa.

FIG. 1 is again illustrative of one method of practicing this invention. Referring to FIG. 1, a feed mixture derived from an HFC-235fa synthesis reactor comprising HF and HFC-235fa, wherein the molar ratio of HF:HFC-235fa is greater than about 2:1, from an HCl removal column (not shown), is passed through line (426) to a multiple stage distillation column (410), operating at a temperature of about 109° C. and a pressure of about 1490 kPa. The bottoms of the distillation column (410), which contains HF at a temperature of about 116° C. and a pressure of about 1500 kPa is removed through line (436) and can be recycled back to the HFC-235fa synthesis reactor. The distillate from column (410) which contains HF/HFC-235fa azeotrope (HF:HFC-235fa molar ratio is about 2:1) is removed from the top of the column (410) and sent through line (435) to column (420). The distillate from column (420) which contains HF/HFC-235fa azeotrope (HF:HFC-235fa molar ratio is about 4:1) and is at a temperature of about 15° C. and a pressure of about 136 kPa is removed from the top of the column (420) and is recycled through line (445) to column (410). The bottoms of the distillation column (420) which contains essentially pure HFC-235fa at about 41° C. and 156 kPa is removed from the bottom of column (420) through line (446). In this embodiment, column (410) operates as a high pressure column. Column (420) operates as a low pressure column.

In another embodiment of this invention the pressures of the columns are reversed. Again referring to FIG. 1, a feed mixture derived from an HFC-235fa synthesis reactor comprising HF and HFC-235fa, wherein the molar ratio of HF:HFC-235fa is about 4:1 or less, from an HCl removal column (not shown), is passed through line (426) to a multiple stage distillation column (410), operating at a temperature of about 29° C. and a pressure of about 146 kPa. The bottoms of the distillation column (410) which contains essentially pure HFC-235fa at about 41° C. and 156 kPa is removed from the bottom of column (410) through line (436). The distillate from column (410) which contains HF/HFC-235fa azeotrope (HF:HFC-235fa molar ratio is about 4:1) at a temperature of about 16° C. and a pressure of about 136 kPa is removed from the top of column (410) and sent through line (435) to column (420). The distillate from column (420) which contains HF/HFC-235fa azeotrope (HF:HFC-235fa molar ratio is about 2:1) and is at at a temperature of about 94° C. and a pressure of about 1450 kPa is removed from the top of column (420) and is recycled through line (445) to column (410). The bottoms of the distillation column (420) which contains HF at a temperature of about 116° C. and a pressure of about 1500 kPa is removed through line (446) and can be recycled back to the HFC-235fa synthesis reactor. In this embodiment column (410) operates as a low pressure column. Column (420) operates as a high pressure column.

While specific temperatures, pressures and molar ratios were recited in the above two embodiments, variation of the pressure will also cause shifts in the HF:HFC-235fa molar ratios and in the distillation temperatures. The use of a "low" and a "high" pressure column in tandem as described above can be used to separate HF from HFC-235fa for any HF:HFC-235fa ratio, e.g., 0.1:1 to 100:1.

The present invention further provides a process for the separation of an azeotropic mixture of hydrogen fluoride (HF) and 1,1,1,3,3,3-hexafluoropropane (i.e., $CF_3CH_2CF_3$ or HFC-236fa) to obtain $CF_3CH_2CF_3$ essentially free of HF. For example, (a) an initial mixture wherein the molar ratio of HF to HFC-236fa is greater than about 0.85:1 can be separated by azeotropic distillation in a first distillation column wherein the temperature of the feed inlet to said distillation column is about 128° C. and the pressure is about 366.2 psia (2524 kPa), with azeotrope products containing HF and HFC-236fa being removed as distillate from the top of the first distillation column and any high boilers and HF being removed from the bottom of the first distillation column; (b) said azeotrope products from the top of the column in step (a) can be fed to a second distillation column wherein the temperature of the feed inlet to said second distillation column is about 4.7° C. and the pressure is about 21.2 psia (146 kPa), with azeotrope products containing HF and HFC-236fa being removed as distillate from the top of the second distillation column; and (c) essentially pure HFC-236fa can be recovered from the bottom of the second distillation column in step (b). Optionally, said azeotrope products containing HF and HFC-236fa removed from the top of the second distillation column can be recycled as feed to step (a).

In another embodiment of this invention, (a) an initial mixture wherein the molar ratio of HF to HFC-236fa is less than about 1.18:1, can be separated by azeotropic distillation in a first distillation column wherein the temperature of the feed inlet to said distillation column is about 4.3° C. and the pressure is about 21.2 psia (146 kPa) with azeotrope products containing HF and HFC-236fa being removed as distillate from the top of the first distillation column; (b) essentially pure HFC-236fa can be recovered from the bottom of the first distillation column; and (c) said azeotrope products from the top of the column in step (a) can be fed to a second distillation column wherein the temperature of the feed inlet to said second distillation column is about 127.9° C. and the pressure is about 364.7 psia (2514 kPa), with azeotrope products containing HF and HFC-236fa being removed as distillate from the top of the second distillation column and any high boilers and HF being removed from the bottom of the second distillation column. Optionally, said azeotrope products containing HF and HFC-236fa from the top of the second distillation column can be recycled as feed to step (a).

The initial mixture of HF and HFC-236fa treated in accordance with the present invention can be obtained from a variety of sources. Generally, the reaction effuents have a molar ratio of HF:HFC-236fa from about 0.1:1 to 100:1. The preferred HF:HFC-236fa molar ratio is from about 0.1:1 to about 10:1 for vapor phase reactions and about 1:1 to about 50:1 for liquid phase reactions to achieve maximum benefit from the instant process. When the initial mixture treated in accordance with the invention also contains HCl and possibly other low-boilers, the HCl and other low-boilers are typically removed in another distillation column before feeding the mixture to the azeotrope separation columns.

High-boilers, if present, can be removed in an independent distillation column after separation of the HF from the HFC-236fa.

FIG. 1 is again illustrative of one method of practicing this invention. Referring to FIG. 1, a feed mixture derived from an HFC-236fa synthesis reactor comprising HF and HFC-236fa, wherein the molar ratio of HF:HFC-236fa is greater than about 0.85:1, from an HCl removal column (not shown), is passed through line (426) to a multiple stage distillation column (410), operating at a temperature of about 127.9° C. and a pressure of about 2514 kPa. The bottoms of the distillation column (410), which contains HF at a temperature of about 140° C. and a pressure of about 2535 kPa is removed through line (436) and can be recycled back to the HFC-236fa synthesis reactor. The distillate from column (410) which contains HF/HFC-236fa azeotrope (HF:HFC-236fa molar ratio is about 0.85:1) is removed from the top of the column (410) and sent through line (435) to column (420). The distillate from column (420) which contains HF/HFC-236fa azeotrope (HF:HFC-236fa molar ratio is about 1.18:1) and is at a temperature of about −0.4° C. and a pressure of about 136 kPa is removed from the top of the column (420) and is recycled through line (445) to column (410). The bottoms of the distillation column (420) which contains essentially pure HFC-236fa at about 9.5° C. and 156 kPa is removed from the bottom of column (420) through line (446). In this embodiment, column (410) operates as a high pressure column. Column (420) operates as a low pressure column.

In another embodiment of this invention the pressures of the columns are reversed. Again referred to FIG. 1, a feed mixture derived from an HFC-236fa synthesis reactor comprising HF and HFC-236fa, wherein the molar ratio of HF:HFC-236fa is about 1.18:1 or less, from an HCl removal column (not shown), is passed through line (426) to a multiple stage distillation column (410), operating at a temperature of about 4.3° C. and a pressure of about 146 kPa. The bottoms of the distillation column (410) which contains essentially pure HFC-236fa is about 9.5° C. and 156 kPa is removed from the bottom of column (410) through line (436). The distillate from column (410) which contains HF/RFC-236fa azeotrope (HF:HFC-236fa molar ratio is about 1.18:1) at a temperature of about −0.4° C. and a pressure of about 136 kPa is removed from the top of column (410) and sent through line (435) to column (420). The distillate from column (420) which contains HF/HFC-236fa azeotrope (HF:HFC-236fa molar ratio is about 0.85:1) and is at a temperature of about 96.7° C. and a pressure of about 2514 kPa is removed from the top of column (420) and is recycled through line (445) to column (410). The bottoms of the distillation column (420) which contains HF at a temperature of about 140° C. and a pressure of about 2535 kPa is removed through line (446) and can be recycled back to the HFC-236fa synthesis reactor. In this embodiment column (410) operates as a low pressure column. Column (420) operates as a high pressure column.

While specific temperatures, pressures and molar ratios were recited in the above two embodiments, variation of the pressure will also cause shifts in the HF:HFC-236fa molar ratios and in the distillation temperatures. The use of a "low" and a "high" pressure column in tandem as described above can be used to separate HF from HFC-236fa for any HF:HFC-236fa ratio, e.g., 0.1:1 to 100:1.

Those skilled in the art will recognize that since the drawings are representational, it will be necessary to include further items of equipment in an actual commercial plant, such as pressure and temperature sensors, pressure relief and control valves, compressors, pumps, storage tanks and the like. The provision of such ancillary items of equipment would be in accordance with conventional chemical engineering practice.

The distillation equipment and its associated feed lines, effluent lines and associated units should be constructed of materials resistant to hydrogen fluoride, hydrogen chloride and chlorine. Typical materials of construction, well-known to the fluorination art, include stainless steels, in particular of the austenitic type, and the well-known high nickel alloys, such as Monel® nickel-copper alloys, Hastelloy® nickel-based alloys and, Inconel® nickel-chromium alloys. Also suitable for reactor fabrication are such polymeric plastics as polytrifluorochloroethylene and polytetrafluoroethylene, generally used as linings.

Without further elaboration, it is believed that one skilled in the art can, using the preceding description, utilize the present invention to its fullest extent. The following preferred specific embodiments are, therefore, to be construed as merely illustrative, and does not constrain the remainder of the disclosure in any way whatsoever.

EXAMPLES

Legend:

ADN is $CN(CH_2)_4CN$  AN is $CH_3CN$
EOAz is 2-ethyl-2-oxazoline  $VCl_2$ is $CH_2=CCl_2$
230fa is $CCl_3CH_2CCl_3$  450jfaf is $CCl_3CH_2CCl_2CH_2CCl_3$
245fa is $CF_3CH_2CHF_2$ The $C_3H_3ClF_4$ isomers are $CHClFCH_2CF_3$ and $CHF_2CH_2CClF_2$.
The $C_3H_3Cl_2F_3$ isomers are $CHCl_2CH_2CF_3$ and $CHClFCH_2CClF_2$.

General Comments

Unless otherwise indicated, the catalyst was $CuCl_2$. When 2-ethyloxazoline was used as an additive, the molar ratio of additive to catalyst was 2:1. The molar ratio of 230fa:450jfaf is reported as the $C_3:C_5$ ratio.

Example 1

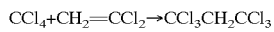

A 400 mL Hastelloy™ C nickel alloy shaker tube was charged with anhydrous cupric chloride (2.18 g, 0.0162 mole), adiponitrile (82.7 g, 0.765 mole), 2-ethyloxazoline (3.2 g, 0.0322 mole), carbon tetrachloride (133.4 g, 0.867 mole), and vinylidene chloride (28.0 g, 0.289 mole). The tube was sealed, cooled in a dry ice bath, evacuated, and purged with nitrogen several times. The tube was placed in a heating jacket and agitation begun. The tube was heated to 120° C. over the course of an hour and then held at 117–120° C. for 0.9 hour; during this time the pressure rose to 59 psig (508 kPa) and then dropped to 56 psig (487 kPa). The tube was then cooled to ambient temperature.

The tube was discharged to afford 236.9 g of a product consisting of a dark red brown liquid layer over a clear yellow supernatant. The top layer (168.7 g) was filtered to yield 1.03 of solid. The filtrate from the top layer and the yellow bottom layer were analyzed by gas chromatography and found to have the compositions (in grams) indicated in Table 1 below.

TABLE 1

| Component | Weight of Components | |
|---|---|---|
| | Top Layer | Bottom Layer |
| ADN | 92.40 | 2.73 |
| VCl2 | — | 0.03 |
| CCl$_4$ | 40.17 | 39.12 |
| 230fa | 29.46 | 22.35 |
| 450jfaf | 4.97 | 3.26 |

Example 2

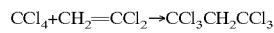

$$CCl_4 + CH_2=CCl_2 \rightarrow CCl_3CH_2CCl_3$$

The reaction procedure was similar to that of Example 1. For runs 1 and 5 to 16, 0.29 moles of vinylidene chloride were charged to the shaker tube. For run 2, 0.09 moles and for runs 3 and 4, 0.58 moles of vinylidene chloride were charged to the shaker tube. For all the runs, 0.87 moles of carbon tetrachloride were used. For run 2, 0.0578 moles of catalyst were used; for all the other runs, 0.0162 moles of catalyst were used. For run 4, the catalyst was cuprous chloride, for all the other runs it was cupric chloride. For runs 5 to 8 and 13 and 14, 44 mL of ADN were charged to the shaker tube; for all the other runs, 87 mL of ADN were used. For runs 3, 4 and 13 to 16, 0.0323 moles of an additive (2-ethyloxazoline) were added to the shaker tube. The ratio of the additive to cooper was 2:1. The results using different conditions are shown in Table 2.

TABLE 2

| Run No. | Temp. °C. | Time hrs. | VCl2 Conv. | % Yield 230fa | C$_3$:C$_5$ Ratio |
|---|---|---|---|---|---|
| 1 | 120 | 2 | 100 | 64.1 | 9.1 |
| 2 | 120 | 2 | 96.3 | 85.7 | 58.3 |
| 3 | 120 | 2 | 99.7 | 58.7 | 6.4 |
| 4 | 120 | 2 | 99.5 | 62.8 | 7.2 |
| 5 | 120 | 1 | 82.4 | 44.2 | 13.9 |
| 6 | 120 | 2 | 93.3 | 61.1 | 14.7 |
| 7 | 140 | 1 | 94.3 | 58.3 | 13.0 |
| 8 | 140 | 2 | 99.6 | 63.3 | 11.3 |
| 9 | 120 | 1 | 100 | 79.6 | 6.4 |
| 10 | 120 | 2 | 100 | 71.1 | 9.2 |
| 11 | 140 | 1 | 100 | 72.3 | 11.2 |
| 12 | 140 | 2 | 99.9 | 78.4 | 11.7 |
| 13 | 120 | 1 | 100 | 61.5 | 7.6 |
| 14 | 140 | 1 | 99.8 | 80.2 | 9.3 |
| 15* | 120 | 1 | 99.9 | 71.6 | 8.7 |
| 16 | 140 | 1 | 99.8 | 66.4 | 11.7 |

*This run represents Example 1 above.

Example 3

Continuous VCl$_2$ Feed

A 600 mL Hastelloy™ C nickel alloy, mechanically stirred, autoclave was charged with 2.42 g (0.0180 mole) of CuCl$_2$ and 1.78 g (0.0180 mole) of CuCl. The autoclave was sealed and leak tested with 200 psig (1480 kPa) nitrogen. The pressure was then vented, the autoclave evacuated, and charged with a mixture consisting of CCl$_4$ (312.1 g, 2.029 moles), adiponitrile (124.6 g, 1.152 moles), CH$_2$=CCl$_2$ (9.81 g, 0.1012 mole), and 2-ethyl oxazoline (7.00 g, 0.0706 mole) from a pressurized cylinder. The pressure of the autoclave was adjusted to 0 psig (101 kPa) with nitrogen and stirring set at 500 rpm. The contents of the autoclave were heated to 119–120° C. for 0.5 hour and then vinylidene chloride was fed to the reactor at a rate of 16 mL per hour for 2.5 hour (48.4 g, 0.499 mole) at 120° C.; during this time the pressure rose to 28 psig (294 kPa). The vinylidene chloride feed was shut off and the autoclave held at 120° C. for another hour; the final pressure was 25 psig (274 kPa). The reactor was cooled to ambient temperature and the bottom layer in the autoclave was discharged via a dip leg (248.1 g); the discharged solution consisted of a yellow liquid with a small amount of a dark layer on top.

The autoclave was then recharged with carbon tetrachloride (240.0 g, 1.56 mole). The autoclave was heated to 120° C. and the vinylidene chloride feed resumed at 16 mL/hr for 2 h; the pressure rose from 28 (294 kPa) to 35 psig (343 kPa). The lower layer was discharged from the reactor as above to afford 283.2 g of product.

In the same manner CCl$_4$ was added three more times to the autoclave (225.6 g, 231.6 g, and 229.4 g) with the bottom layer from the autoclave discharged between additions (271.0 g, 280.5 g, 204.0 g, respectively). The total amount of vinylidene chloride fed was 2.20 moles. The top layers from the autoclave were combined to give 259.4 g and 2.3 of solid. The overall yield of 1,1,1,3,3,3-hexachloropropane was about 89.5% with a vinylidene chloride conversion of 86.4%; the overall ratio of 1,1,1,3,3,3-hexachloropropane to 1,1,1,3,3,5,5,5-octachloropentane was about 18.5.

The five bottom layers and the combined top layers from the reactor were analyzed by a calibrated gas chromatograph. The weights of the primary solution components are given below.

| | Weight of Products, grams | | | | | |
|---|---|---|---|---|---|---|
| | Bottom Layers from Reactor | | | | | |
| Component | No. 1 | No. 2 | No. 3 | No. 4 | No. 5 | Top |
| CH$_2$=CCl$_2$ | 1.6 | 4.2 | 6.9 | 7.9 | 7.9 | 0.4 |
| CCl$_4$ | 152.5 | 179.8 | 179.9 | 194.2 | 186.0 | 50.5 |
| CCl$_3$CH$_2$CCl$_3$ | 86.9 | 83.9 | 79.4 | 75.4 | 71.4 | 28.9 |
| Cl(CCl$_2$CH$_2$)$_2$CCl$_3$ | 6.5 | 5.9 | 6.3 | 6.0 | 5.5 | 1.7 |
| Adiponitrile | 4.2 | 4.2 | 4.5 | 4.5 | 5.2 | 124.0 |

Example 4

Continuous VCl$_2$ Feed

Following a procedure similar to that of Example 3, a 600 mL Hastelloy-C nickel alloy, mechanically stirred, autoclave was charged with 2.42 g (0.0180 mole) of CuCl$_2$ and 1.78 g (0.0180 mole) of CuCl. The autoclave was sealed and then charged with a mixture consisting of CCl$_4$ (309.1 g, 2.01 moles), adiponitrile (189.3 g, 1.75 moles), and CH$_2$=CCl$_2$ (9.94 g, 0.102 mole) from a pressurized cylinder. The pressure of the autoclave was adjusted to 0 psig (101 kPa) with nitrogen and stirring set at 500 rpm. The contents of the autoclave were heated to 119–120° C. for 0.5 hour and then vinylidene chloride was fed to the reactor at a rate of 16 mL per hour for 2 hours (38.7 g, 0.400 mole) at 120° C.; during this time the pressure rose to 43 psig (398 kPa). The vinylidene chloride feed was shut off and the autoclave held at 120° C. for another 0.5 hour; the final pressure was 39 psig (370 kPa). The reactor was cooled to ambient temperature and the bottom layer in the autoclave was discharged via a dip leg (184.7 g); the discharged solution consisted of a yellow liquid with a small amount of a dark layer on top.

The autoclave was then recharged with carbon tetrachloride (198.5 g, 1.29 mole). The autoclave was heated to 120° C. and the vinylidene chloride feed resumed at 16 mL/hr for 2 hours; the pressure rose from 29 (301 kPa) to 38 psig (363 kPa). The lower layer was discharged from the reactor as above to afford 234.8 g of product.

In the same manner $CCl_4$ was added four more times to the autoclave (191.4 g, 194.3 g, 201.2, and 192.0 g) with the bottom layer from the autoclave discharged between additions (232.1 g, 231.9 g, 246.9 g, and 230.6, respectively). The total amount of vinylidene chloride fed was 2.47 moles. The top layers from the autoclave were combined to give 286.5 g and 2.3 of solid. The overall yield of 1,1,1,3,3,3-hexachloropropane was about 88.5% with a vinylidene chloride conversion of 85.0%; the overall ratio of 1,1,1,3,3,3-hexachloropropane to 1,1,1,3,3,5,5,5-octachloropentane was about 21.

The six bottom layers and the combined top layer from the reactor were analyzed by a calibrated gas chromatograph. The weights of the primary solution components are given below.

| | Weight of Products, grams | | | | | | |
|---|---|---|---|---|---|---|---|
| | Bottom Layers from Reactor | | | | | | |
| Component | No. 1 | No. 2 | No. 3 | No. 4 | No. 5 | No. 6 | Top |
| $CH_2=CCl_2$ | 8.1 | 5.7 | 4.7 | 1.2 | 4.3 | 6.4 | 5.4 |
| $CCl_4$ | 127.1 | 145.0 | 131.1 | 121.5 | 138.2 | 148.5 | 92.8 |
| $CCl_3CH_2CCl_3$ | 42.1 | 74.1 | 77.2 | 75.0 | 75.4 | 69.2 | 52.6 |
| $Cl(CCl_2CH_2)_2CCl_3$ | 2.2 | 4.9 | 5.5 | 5.1 | 5.1 | 5.0 | 3.0 |
| Adiponitrile | 2.9 | 3.8 | 4.6 | 4.0 | 4.2 | 4.0 | 177.4 |

Example 5

Continuous $VCl_2$ Feed

Propylene Carbonate Solvent with 2EOAz

Following a procedure similar to Example 3, a 600 mL Hastelloy™ C nickel alloy, mechanically stirred, autoclave was charged with 2.42 g (0.0180 mole) of $CuCl_2$ and 1.78 g (0.0180 mole) of CuCl. The autoclave was sealed and then charged with a mixture consisting of $CCl_4$ (301.0 g, 1.96 moles), propylene carbonate (134.4 g, 1.32 moles), 2-ethyloxazoline (6.91 g, 0.0697 mole) and $CH_2=CCl_2$ (9.68 g, 0.0998 mole) from a pressurized cylinder. The pressure of the autoclave was adjusted to 0 psig (101 kPa) with nitrogen and stirring set at 500 rpm. The contents of the autoclave were heated to 119–120° C. for 0.5 hour and then vinylidene chloride was fed to the reactor at a rate of 16 mL per hour for 2 hours (38.7 g, 0.400 mole) at 120° C.; during this time the pressure rose to a maximum of 25 psig (274 kPa) and then dropped to 22 psig (253 kPa). The vinylidene chloride feed was shut off and the autoclave held at 120° C. for another 0.5 hour; the final pressure was 21 psig (246 kPa). The reactor was cooled to ambient temperature and the bottom layer in the autoclave was discharged via a dip leg (147.7 g); the discharged solution consisted of an amber liquid with a small amount of a dark layer on top.

The autoclave was then recharged with carbon tetrachloride (183.3 g, 1.19 mole). The autoclave was heated to 120° C. and the vinylidene chloride feed resumed at 16 mL/hr for 2 hours; the pressure rose from 22 (253 kPa) to 29 psig (301 kPa). The lower layer was discharged from the reactor as above to afford 310.3 g of product.

In the same manner $CCl_4$ was added four more times to the autoclave (200.5 g, 197.8 g, 200.3, and 205.8 g) with the bottom layer from the autoclave discharged between additions (302.5 g, 277.1 g, 261.2 g, and 255.7, respectively). The total amount of vinylidene chloride fed was 2.50 moles. The top layers from the autoclave were combined to give 144.3 g and 0.3 of solid. The overall yield of 1,1,1,3,3,3-hexachloropropane was about 84.3% with a vinylidene chloride conversion of 86.1%; the overall ratio of 1,1,1,3,3,3-hexachloropropane to 1,1,1,3,3,5,5,5-octachloropentane was about 18.

The six bottom layers and the combined top layer from the reactor were analyzed by a calibrated gas chromatograph. The weights of the primary solution components are given below.

| | Weight of Products, grams | | | | | | |
|---|---|---|---|---|---|---|---|
| | Bottom Layers from Reactor | | | | | | |
| Component | No. 1 | No. 2 | No. 3 | No. 4 | No. 5 | No. 6 | Top |
| $CH_2=CCl_2$ | 0.3 | 1.0 | 2.1 | 2.5 | 7.1 | 16.6 | 3.8 |
| $CCl_4$ | 82.3 | 165.4 | 157.6 | 142.8 | 143.8 | 190.8 | 38.7 |
| $CCl_3CH_2CCl_3$ | 48.4 | 106.4 | 104.7 | 89.9 | 69.3 | 30.2 | 6.4 |
| $Cl(CCl_2CH_2)_2CCl_3$ | 1.8 | 5.1 | 5.9 | 6.4 | 12.8 | 11.7 | 2.3 |
| Propylene Carbonate | 11.1 | 24.4 | 21.4 | 15.5 | 11.1 | 9.4 | 36.5 |

Example 6

$$CCl_4 + CH_2=CH_2 \rightarrow CCl_3CH_2CH_2Cl$$

A 400 mL Hastelloy™ C nickel alloy shaker tube was charged with anhydrous cupric chloride (2.18 g, 0.0162 mole), adiponitrile (82.7 g, 0.765 mole), and carbon tetrachloride (133.4 g, 0.867 mole). The tube was sealed, cooled in a dry ice bath, evacuated, and purged with nitrogen. The tube was evacuated once more and charged with 12 g (0.43 mole) of ethylene. The tube was placed in a heating jacket and agitation begun. The tube was heated to 120–121° C. over the course of 2 hours. During this time, the pressure rose to 521 psig (3693 kPa) and dropped steadily to 288 psig (2086 kPa). The tube was allowed to cool overnight and was vented and purged the next morning. The product was discharged to afford 224.4 g of a dark red brown liquid layer over an amber lower liquid layer.

GC analysis of the layers indicated the following compositions:

| | GC Area % | |
|---|---|---|
| Component | Top Layer | Bottom Layer |
| $CCl_4$ | 1.3 | 26.1 |
| $CHCl=CCl_2$ | 0.04 | 0.3 |
| $CCl_3CH_2CH_3$ | 0.3 | 2.6 |
| $CCl_2=CCl_2$ | 0.2 | 1.8 |
| $CCl_3CH_2CH_2Cl$ | 9.1 | 51.3 |
| Adiponitrile | 86.9 | 11.2 |
| $CCl_3(CH_2CH_2)_2Cl$ | 0.9 | 3.7 |

Example 7

CCl₄+trans-CHCl=CHCl→CCl₃CHClCHCl₂

Following a procedure similar to Example 6, a 400 mL Hastelloy™ C nickel alloy shaker tube was charged with anhydrous cupric chloride (2.18 g, 0.0162 mole), adiponitrile (82.7 g, 0.765 mole), carbon tetrachloride (133.4 g, 0.867 mole), and trans-1,2-dichloroethylene (28.0 g, 0.289 mole). The tube was heated to 128–129° C. over the course of 4.1 hours; the pressure range was 93–97 psig (742–770 kPa).

The tube was cooled overnight and was vented and purged the next morning. The product was discharged to afford 235.94 g of a dark red brown top liquid layer over a yellow lower liquid layer.

GC analysis of the layers indicated the following compositions:

| | GC Area % | |
|---|---|---|
| Component | Top Layer | Bottom Layer |
| trans-CHCl=CHCl | 6.4 | 38.6 |
| cis-CHCl=CHCl | 0.1 | 0.3 |
| CHCl₃ | 0.03 | 0.09 |
| CCl₄ | 3.9 | 45.5 |
| CHCl=CCl₂ | 0.01 | 0.1 |
| CCl₂=CCl₂ | 0.03 | 0.4 |
| CHCl₂CCl=CCl₂ | 0.3 | 2.5 |
| Adiponitrile | 88.3 | 9.9 |
| CCl₃CHClCHCl₂ | 0.9 | 3.7 |

Example 8

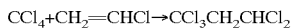
CCl₄+CH₂=CHCl→CCl₃CH₂CHCl₂

Following a procedure similar to Example 6, a 400 mL Hastelloy™ C nickel alloy shaker tube was charged with anhydrous cupric chloride (2.18 g, 0.0162 mole), adiponitrile (82.7 g, 0.765 mole), and carbon tetrachloride (133.4 g, 0.867 mole). The tube was cooled in dry ice, evacuated, purged with nitrogen, re-evacuated and charged with vinyl chloride (9 g, 0.14 mole). The tube was heated to 128–130° C. over the course of 4.1 hours; during this time the pressure decreased from 86 psig (694 kPa) to 45 psig (412 kPa).

The tube was cooled overnight and was vented and purged the next morning. The product was discharged to afford 223.5 g of a dark red brown top liquid layer over a yellow lower liquid layer.

GC analysis of the layers indicated the following compositions:

| | GC Area % | |
|---|---|---|
| Component | Top Layer | Bottom Layer |
| CCl₄ | 4.2 | 33.3 |
| CCl₃CH₂CHCl₂ | 9.9 | 52.2 |
| Adiponitrile | 84.0 | 9.5 |
| CCl₃(CH₂CHCl)₂Cl | 0.7 | 2.8 |
| CCl₃(CH₂CHCl)₃Cl(2) | 0.06 | 0.2 |

Example 9

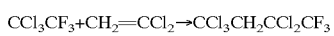
CCl₃CF₃+CH₂=CCl₂→CCl₃CH₂CCl₂CF₃

Following a procedure similar to Example 7, a 400 mL Hastelloy™ C nickel alloy shaker tube was charged with anhydrous cupric chloride (2.18 g, 0.0162 mole), adiponitrile (82.7 g, 0.765 mole), 1,1,1-trichlorotrifluoroethane (162.5 g, 0.867 mole), and vinylidene chloride (28.0 g, 0.289 mole). The tube was heated to 127–132° C. over the course of 3.1 hours; the pressure dropped from 141 psig (1073 kPa) initially to 124 psig (956 kPa) during the reaction.

The tube was cooled overnight and was vented and purged the next morning. The product was discharged to afford 256.7 g of a dark red brown top liquid layer over an amber lower liquid layer.

GC analysis of the layers indicated the following compositions:

| | GC Area % | |
|---|---|---|
| Component | Top Layer | Bottom Layer |
| CF₃CCl₂F | 0.04 | 1.5 |
| CH₂=CCl₂ | 2.4 | 9.7 |
| CF₃CCl₃ | 4.4 | 74.8 |
| CF₃CCl₂CH₂CCl₃ | 1.2 | 8.2 |
| Adiponitrile | 90.9 | 1.5 |
| CF₃CCl₂(CH₂CCl₂)₂Cl | 0.5 | 2.8 |
| CF₃CCl₂(CH₂CCl₂)₃Cl | 0.1 | 0.4 |

Example 10

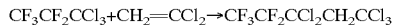
CF₃CF₂CCl₃+CH₂=CCl₂→CF₃CF₂CCl₂CH₂CCl₃

Following a procedure similar to Example 7, a 400 mL Hastelloy™ C nickel alloy shaker tube was charged with anhydrous cupric chloride (2.18 g, 0.0162 mole), adiponitrile (82.7 g, 0.765 mole), 1,1,1-trichloropentafluoropropane (102.8 g, 0.433 mole), and vinylidene chloride (28.0 g, 0.289 mole). The tube was heated to 128–133° C. over the course of 3.1 h; the pressure dropped from a high of 112 psig (873 kPa) initially to 72 psig (598 kPa) at the end of the reaction.

The tube was cooled overnight and vented and purged the next morning. The product was discharged to afford 205.9 g of a dark red brown top liquid layer over a dark orange lower liquid layer; some brown insolubles were observed in the bottom of the jar.

GC analysis of the layers indicated the following compositions:

| | GC Area % | |
|---|---|---|
| Component | Top Layer | Bottom Layer |
| CH₂=CCl₂ | 0.1 | 0.3 |
| CF₃CF₂CCl₃ | 1.3 | 49.7 |
| CF₃CF₂CCl₂CH₂CCl₃ | 1.6 | 33.1 |
| Adiponitrile | 95.5 | 1.4 |
| CF₃CF₂CCl₂(CH₂CCl₂)₂Cl | 0.6 | 9.1 |
| Higher oligomers (3) | 0.1 | 3.1 |

Example 11

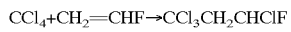
CCl₄+CH₂=CHF→CCl₃CH₂CHClF

Following a procedure similar to Example 6, a 400 mL Hastelloy™ C nickel alloy shaker tube was charged with anhydrous cupric chloride (2.18 g, 0.0162 mole), adiponitrile (82.7 g, 0.765 mole), and carbon tetrachloride (133.4 g, 0.867 mole). The tube was cooled in dry ice, evacuated, purged with nitrogen, re-evacuated and charged with vinyl fluoride (7 g, 0.15 mole). The tube was heated to 119–120° C. over the course of 2.1 hours; during this time the pressure decreased from 174 psig (1301 kPa) to 121 psig (935 kPa).

The tube was cooled overnight and vented and purged the next morning. The product was discharged to afford 212.8 g of a dark red brown top liquid layer over a almost colorless lower liquid layer.

GC analysis of the layers indicated the following compositions:

|  | GC Area % | |
| --- | --- | --- |
| Component | Top Layer | Bottom Layer |
| CHCl$_3$ | 0.03 | 0.1 |
| CCl$_4$ | 3.8 | 62.7 |
| CCl$_3$CH$_2$CHClF | 2.8 | 20.1 |
| CCl$_3$CHFCH$_2$Cl | 0.2 | 1.4 |
| Adiponitrile | 91.7 | 10.2 |
| Oligomers (2) | 0.2 | 0.6 |

Example 12

CCl$_3$CH$_2$CCl$_3$+CH$_2$=CCl$_2$→CCl$_3$(CH$_2$CCl$_2$)$_2$Cl

Following a procedure similar to Example 7, a 400 mL Hastelloy™ C nickel alloy shaker tube was charged with anhydrous cupric chloride (2.18 g, 0.0162 mole), adiponitrile (82.7 g, 0.765 mole), 1,1,1,3,3,3-hexachloropropane (144.9 g, 0.578 mole), and vinylidene chloride (28.0 g, 0.289 mole). The tube was heated to 137–140° C. over the course of 2.9 hours; the pressure dropped from 38 psig (363 kPa) initially to 16 psig (212 kPa) at the end of the experiment.

The tube was cooled overnight and vented and purged the next morning. The product was discharged to afford 243.1 g of a dark red brown top liquid layer over a dark red brown lower liquid layer.

GC analysis of the layers indicated the following compositions:

|  | GC Area % | |
| --- | --- | --- |
| Component | Top Layer | Bottom Layer |
| CH$_2$=CCl$_2$ | 2.6 | 2.5 |
| Adiponitrile | 68.8 | 28.6 |
| CCl$_3$CH$_2$CCl$_3$ | 19.9 | 47.9 |
| CCl$_3$(CH$_2$CCl$_2$)$_2$Cl | 7.4 | 19.4 |

Example 13

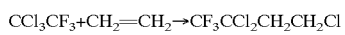

CCl$_3$CF$_3$+CH$_2$=CH$_2$→CF$_3$CCl$_2$CH$_2$CH$_2$Cl

Following a procedure similar to Example 6, a 400 mL Hastelloy™ C nickel alloy shaker tube was charged with anhydrous cupric chloride (2.18 g, 0.0162 mole), adiponitrile (82.7 g, 0.765 mole), and 1,1,1-trichlorotrifluoroethane (108.3 g, 0.578 mole). The tube was sealed, cooled in a dry ice bath, evacuated, and purged with nitrogen. The tube was evacuated once more and charged with 12 g (0.43 mole) of ethylene. The tube was placed in the autoclave and agitation begun. The tube was heated to 129–131° C. over the course of 2 hours. During this time, the pressure rose to 665 psig (4685 kPa) and dropped steadily to 564 psig (3989 kPa). The tube was cooled overnight and vented and purged the next morning. The product was discharged to afford 178.2 g of a brown liquid layer over an pale yellow lower liquid layer.

GC analysis of the layers indicated the following compositions:

|  | GC Area % | |
| --- | --- | --- |
| Component | Top Layer | Bottom Layer |
| CF$_3$CCl$_2$F | 0.002 | 0.2 |
| CF$_3$CCl$_3$ | 1.2 | 62.0 |
| CF$_3$CCl$_2$CH$_2$CH$_2$Cl | 1.4 | 17.6 |
| CF$_3$CCl$_2$(CH$_2$CH$_2$)$_2$Cl | 1.2 | 8.6 |
| Adiponitrile | 94.1 | 1.8 |

Example 14

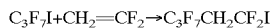

C$_3$F$_7$I+CH$_2$=CF$_2$→C$_3$F$_7$CH$_2$CF$_2$I

Following a procedure similar to Example 6, a 400 mL Hastelloy™ C nickel alloy shaker tube was charged with anhydrous cupric chloride (2.18 g, 0.0162 mole), adiponitrile (82.7 g, 0.765 mole), and 1-iodoheptafluoropropane (100 g, 0.338 mole). The tube was sealed, cooled in a dry ice bath, evacuated, and purged with nitrogen. The tube was evacuated once more and charged with 12.8 g (0.20 mole) of vinylidene fluoride. The tube was placed in the autoclave and agitation begun. The tube was heated to 129–130° C. over the course of 4 hours. During this time, the pressure rose to 366 psig (2624 kPa) and dropped steadily to 312 psig (2252 kPa).

The tube was cooled overnight and vented and purged the next morning. The product was discharged to afford 160.6 g of a brown liquid layer over an yellow lower liquid layer.

GC analysis of the layers indicated the following compositions:

|  | GC Area % | |
| --- | --- | --- |
| Component | Top Layer | Bottom Layer |
| C$_3$F$_7$I | 1.8 | 3.8 |
| C$_3$F$_7$CH$_2$CF$_2$Cl | 0.2 | 4.1 |
| C$_3$F$_7$(CH$_2$CF$_2$)$_2$Cl | 0.09 | 0.1 |
| C$_3$F$_7$CH$_2$CF$_2$I | 2.5 | 24.0 |
| C$_3$F$_7$CF$_2$CH$_2$I | 0.02 | 0.3 |
| C$_3$F$_7$(CH$_2$CF$_2$)$_2$I | 0.8 | 3.9 |
| C$_3$F$_7$CH$_2$CF$_2$CH$_2$I | 0.05 | 0.4 |
| Adiponitrile | 93.9 | 19.3 |

Example 15

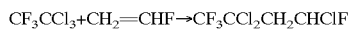

CF$_3$CCl$_3$+CH$_2$=CHF→CF$_3$CCl$_2$CH$_2$CHClF

Following a procedure similar to Example 6, a 400 mL Hastelloy™ C nickel alloy shaker tube was charged with anhydrous cupric chloride (2.18 g, 0.0162 mole), adiponitrile (82.7 g, 0.765 mole), and 1,1,1-trichlorotrifluoroethane (108.3 g, 0.578 mole). The tube was cooled in dry ice, evacuated, purged with nitrogen, re-evacuated and charged with vinyl fluoride (10 g, 0.22 mole). The tube was heated to 129–131° C. over the course of 2.9 hours; during this time the pressure decreased from 393 psig (2810 kPa) to 304 psig (2197 kPa). The tube was cooled overnight and vented and purged the next morning. The product was discharged to afford 178.6 g of a dark red brown top liquid layer over a pale yellow lower liquid layer.

GC analysis of the layers indicated the following compositions:

| Component | GC Area % | |
|---|---|---|
| | Top Layer | Bottom Layer |
| $CF_3CCl_3$ | 3.2 | 81.7 |
| $CF_3CCl_2CH_2CHClF$ | 1.7 | 13.0 |
| Oligomers (2) | 0.8 | 1.8 |
| Adiponitrile | 92.8 | 1.1 |

Example 16

$CCl_3CH_2CCl_3 + HF \rightarrow CF_3CH_2CF_3$

To a 450 mL Hastelloy™ C nickel alloy autoclave provided with an agitator, condenser operating at −15° C. and a back-pressure regulator was charged 120 g (0.48 mole) $CCl_3CH_2CCl_3$ (230fa), prepared by the method of this invention (Examples 1 to 5) and 24 g (0.087 mole) of TaF5. The autoclave was sealed and cooled in dry-ice. Into the chilled autoclave was condensed 120 g (6.0 moles) of anhydrous HF. The back-pressure regulator was set to 500 psig (3548 kPa). The autoclave and contents were brought to room temperature and heated with stirring at 75° C. (internal temperature) for one hour and at 125°–130° C. for two hours using an electrical heater. After this period, the autoclave and contents were brought to room temperature and near atmospheric pressure. A vapor sample was withdrawn and analyzed by gas chromatography. Area % analysis indicated 96% 236fa ($CF_3CH_2CF_3$), 2% 235fa ($CF_3CH_2CF_2Cl$) and 2% other products.

Example 17

$CCl_3CH_2CCl_3 + HF \rightarrow CF_3CH_2CF_3$

Example 16 was substantially repeated except that the amount of 230fa charged was 150 g (0.6 mole), TaF5 charged was 3.3 g (0.012 mole) and anhydrous HF charged was 150 g (7.5 moles). Analysis indicated 72% 236fa and 27% 235fa.

Example 18

$CCl_3CH_2CCl_3 + HF \rightarrow CF_3CH_2CF_3$

Example 16 was substantially repeated except that the catalyst was $SbCl_5$ (0.087 mole, 26 g) and the autoclave and contents were maintained at about 70° C. for two hours before raising the temperature to 125°–130° C. Analysis indicated 88% 236fa and 12% 235fa.

Example 19

$CCl_3CH_2CCl_3 + HF \rightarrow CF_3CH_2CCl_2F$

Example 16 was substantially repeated except that the catalyst was $MoCl_5$ (20 g, 0.087 mole) and the autoclave and contents were maintained at 80° C. for three hours and the temperature was not raised any further. Analysis indicated 4% 236fa, 11% 235fa and 76% $CF_3CH_2CCl_2F$ (234fb) in addition to small amounts of other products.

Example 20

$CCl_3CH_2CHCl_2 + HF \rightarrow CF_3CH_2CHF_2$

A 160 mL Hastelloy™ C nickel alloy Parr reactor equipped with a magnetically driven agitator, pressure transducer, vapor phase sampling valve, thermal well, and valve was charged with 10.5 g (0.039 mole) $NbCl_5$ in a dry box. The autoclave was then removed from the drybox; 50 g (2.5 moles) of HF were added to the autoclave via vacuum transfer. The autoclave was brought to 14° C. and charged with 10.5 g (0.048 mole) of $CCl_3CH_2CHCl_2$ (prepared according to the procedure described in Example 8 above) via a cylinder pressurized with nitrogen. The autoclave was then heated with stirring; within 19 minutes the pressure reached 516 psig (3658 kPa) at 120° C. The temperature was held at 120° C. for 16 minutes. A sample of the reactor vapor at this point had the following composition:

| Component | GC Area % |
|---|---|
| $CF_3CH_2CHF_2$ | 84.6 |
| $CF_3CH=CHCl$ | 0.6 |
| $C_3H_3ClF_4$ isomers | 4.9 |
| $C_3H_3Cl_2F_3$ isomers | 6.8 |

Examples 21 and 22

In the following two examples, all values for the compounds are in moles and temperatures are in Celsius. The data were obtained by calculation using measured and calculated thermodynamic properties. The numbers at the top of the columns refer to FIG. 1.

Example 21

| Compound | 426 Feed Mixture | 435 HP Col. Dist. | 436 HF | 445 HF/245fa Recycle | 446 245fa Prod. |
|---|---|---|---|---|---|
| HF | 66.7 | 97.2 | 66.7 | 97.2 | — |
| 245fa | 33.3 | 79.0 | — | 45.7 | 33.3 |
| Temp. ° C. | 75 | 79 | 104 | 12 | 27 |
| Press. kPa | 1135 | 1135 | 1156 | 136 | 156 |

Example 22

| Compound | 426 Feed Mixture | 435 LP Col. Dist. | 436 245fa Prod. | 445 HP Col. Dist. | 446 HF |
|---|---|---|---|---|---|
| HF | 50.0 | 118.5 | — | 68.5 | 50 |
| 245fa | 50.0 | 55.7 | 50.0 | 55.7 | — |
| Temp. ° C. | 10 | 12 | 27 | 79 | 104 |
| Press. kPa | 136 | 136 | 156 | 1135 | 1156 |

Examples 23 and 24

In the following two examples, all values for the compounds are in moles and temperatures are in Celsius. The data were obtained by calculation using measured and calculated thermodynamic properties. The numbers at the top of the columns refer to FIG. 1.

Example 23

| Compound | 426 Feed Mixture | 435 HP Col. Dist. | 436 HF | 445 HF/235fa Recycle | 446 235fa Prod. |
|---|---|---|---|---|---|
| HF | 90 | 40 | 90 | 40 | — |
| 235fa | 10 | 20 | — | 10 | 10 |
| Temp. ° C. | 75 | 94 | 116 | 16 | 41 |
| Press. kPa | 1135 | 1480 | 1500 | 136 | 156 |

Example 24

| Compound | 426 Feed Mixture | 435 LP Col. Dist. | 436 245fa Prod. | 445 HP Col. Dist. | 446 HF |
|---|---|---|---|---|---|
| HF | 50 | 100 | — | 50 | 50 |
| 235fa | 50 | 25 | 50 | 25 | — |
| Temp. ° C. | 10 | 16 | 41 | 94 | 116 |
| Press. kPa | 136 | 136 | 156 | 1480 | 1500 |

Examples 25 and 26

In the following two examples, all values for the compounds are in moles and temperatures are in Celsius. The data were obtained by calculation using measured and calculated thermodynamic properties. The numbers at the top of the columns refer to FIG. 1.

Example 25

| Compound | 426 Feed Mixture | 435 HP Col. Dist. | 436 HF | 445 HF/236fa Recycle | 446 236fa Prod. |
|---|---|---|---|---|---|
| HF | 83.3 | 51.1 | 83.3 | 51.1 | — |
| 236fa | 16.7 | 60.1 | — | 43.4 | 16.7 |
| Temp. ° C. | 75 | 96.7 | 140 | −0.4 | 9.5 |
| Press. kPa | 2514 | 2514 | 2535 | 136 | 156 |

Example 26

| Compound | 426 Feed Mixture | 435 LP Col. Dist. | 436 245fa Prod. | 445 HF Col. Dist. | 446 HF |
|---|---|---|---|---|---|
| HF | 33.3 | 120.1 | — | 86.7 | 33.3 |
| 236fa | 66.7 | 102.1 | 66.7 | 102.1 | — |
| Temp. ° C. | 10 | −0.4 | 9.5 | 96.7 | 140 |
| Press. kPa | 136 | 136 | 156 | 2514 | 2535 |

What is claimed is:

1. A process for producing $CF_3CH_2CHF_2$, comprising:
   fluorinating $CCl_3CH_2CHCl_2$ with HF to produce a fluorination product comprising $CF_3CH_2CHF_2$ and HF;
   obtaining an azeotropic mixture of $CF_3CH_2CHF_2$ with HF from the fluorination product; and
   purifying $CF_3CH_2CHF_2$ from said mixture.

2. The process of claim 1 wherein the azeotropic mixture comprises (a) from about 44 to 84 mole percent HF and (b) from about 56 to 16 mole percent $CF_3CH_2CHF_2$, and exhibits a relative volatility of about 1 at a pressure within the range of 5.5 kPa to 3850 kPa when the temperature is adjusted within the range of −50° C. to 130° C.

3. The process of claim 2 wherein the azeotropic mixture is distilled in a high pressure distillation column to yield an azeotropic distillate of HF and $CF_3CH_2CHF_2$ and a bottoms containing HF; and wherein the azeotropic distillate is further distilled in a low pressure distillation column to yield another azeotropic distillate of HF and $CF_3CH_2CHF_2$ and a bottoms of essentially pure $CF_3CH_2CHF_2$.

4. The process of claim 2 wherein the azeotropic mixture is distilled in a low pressure distillation column to yield an azeotropic distillate of HF and $CF_3CH_2CHF_2$ and a bottoms containing essentially pure $CF_3CH_2CHF_2$; and wherein the azeotropic distillate is further distilled in a high pressure distillation column to yield another azeotropic distillate of HF and $CF_3CH_2CHF_2$ and a bottoms containing HF.

5. The process of claim 2 wherein the $CCl_3CH_2CHCl_2$ is produced by reacting $CCl_4$ with $CH_2$=CHCl.

6. The process of claim 5 wherein the $CCl_4$ is reacted with the $CH_2$=CHCl in a dinitrile or cyclic carbonate ester solvent which divides the reaction mixture into two liquid phases, and in the presence of a catalyst system containing (i) at least one catalyst selected from the group consisting of monovalent and divalent copper and (ii) a promoter selected from aromatic and aliphatic heterocyclic compounds which contain at least one carbon-nitrogen double bond in the heterocyclic ring.

* * * * *